(12) United States Patent
Patil et al.

(10) Patent No.: US 7,473,366 B2
(45) Date of Patent: Jan. 6, 2009

(54) PROCESS FOR THE PURIFICATION OF MACROLIDES

(75) Inventors: Nitin Sopanrao Patil, Karnataka (IN); Rakesh Mendhe, Karnataka (IN); Anand Prakash Khedkar, Karnataka (IN); Ramakrishnan Melarkode, Karnataka (IN); Ramavana Gururaja, Karnataka (IN)

(73) Assignee: BioCon Limited, Karnataka (IN)

( * ) Notice: Subject to any disclaimer, the term of this patent is extended or adjusted under 35 U.S.C. 154(b) by 290 days.

(21) Appl. No.: 10/596,227

(22) PCT Filed: Dec. 5, 2003

(86) PCT No.: PCT/IN03/00383

§ 371 (c)(1),
(2), (4) Date: Jun. 5, 2006

(87) PCT Pub. No.: WO2005/054253

PCT Pub. Date: Jun. 16, 2005

(65) Prior Publication Data

US 2007/0173642 A1  Jul. 26, 2007

(51) Int. Cl.
*B01D 15/08* (2006.01)

(52) U.S. Cl. .................... 210/635; 210/656; 210/198.2; 540/456; 540/458; 549/263

(58) Field of Classification Search ................. 210/635, 210/656, 659, 198.2; 540/456, 458; 549/263
See application file for complete search history.

(56) References Cited

U.S. PATENT DOCUMENTS

| 4,734,492 | A  |   | 3/1988  | Tanba et al. |   |
|---|---|---|---|---|---|
| 4,894,366 | A  |   | 1/1990  | Okuhara et al. |   |
| 5,508,398 | A  |   | 4/1996  | Gletsos |   |
| 5,616,595 | A  |   | 4/1997  | Chu et al. |   |
| 6,423,233 | B1 | * | 7/2002  | Keri et al. | 210/659 |
| 6,444,452 | B1 | * | 9/2002  | Keri et al. | 435/135 |
| 6,492,513 | B1 |   | 12/2002 | Nishihara et al. |   |
| 6,521,762 | B2 | * | 2/2003  | Keri et al. | 549/292 |
| 6,576,135 | B1 |   | 6/2003  | Higaki et al. |   |
| 6,706,192 | B2 | * | 3/2004  | Keri et al. | 210/659 |
| 7,220,357 | B2 | * | 5/2007  | Keri et al. | 210/635 |
| 2003/0166924 | A1 | * | 9/2003 | Keri et al. | 540/458 |
| 2008/0000834 | A1 | * | 1/2008 | Cvak et al. | 210/635 |

FOREIGN PATENT DOCUMENTS

EP  0 184 162 B1  4/1994

OTHER PUBLICATIONS

Sanglier JJ et al, "Sanglifehrins A, B, C and D, novel cyclophilin-binding compounds isolated from *streptomyces* sp. A92-308110. I. Taxonomy, fermentation, isolation and biological activity" J Antibiot (Tokyo). May 1999;52(5):466-73.

Weizheng Wang-Fan et al, "Application of centrifugal counter-current chromatography to the separation of macrolide antibiotic analogues I. Selection of solvent systems based on solubility and partition coeffecient investigations" Journal of Chromatography A, 864 (1999) 69-76.

* cited by examiner

*Primary Examiner*—Ernest G Therkorn
(74) *Attorney, Agent, or Firm*—Caesar, Rivise, Bernstein, Cohen & Pokotilow, Ltd.

(57) ABSTRACT

The invention relates to a process for the recovery of a macrolide in substantial pure form including:
a) treating an impure or crude macrolide with water immiscible solvent to form a mixture,
b) optionally concentrating the mixture,
c) treating with ammonia gas to phase out impurities,
d) separating impurities,
e) optionally concentrating a phase containing the macrolide,
f) loading on silica gel chromatography, optionally reversed phase or pretreated with silver, and eluting the macrolide,
g) affording the macrolide in the substantially pure form,
h) optional repetition of steps f and g to afford the macrolide in the substantially pure form. The macrolide is preferably tacrolimus, immunomycin or sirolimus.

10 Claims, No Drawings

PROCESS FOR THE PURIFICATION OF MACROLIDES

FIELD OF THE INVENTION

This invention relates to a novel process for purification of macrolides.

BACKGROUND OF THE INVENTION

A compound, 15,19-Epoxy-3H-pyrido[2,1-c][1,4]oxaazacyclotricosine-1,7,20,21(4H,23H)-tetrone, 5,6,8,11,12,13,14,15,16,17,18,19,24,25,26,26a-hexadecahydro-5,19-dihydroxy-3-[(1E)-2-[(1R,3R,4R)-4-hydroxy-3-methoxycyclohexyl]-1-methyl ethenyl]-14,16-dimethoxy-4,10,12,18-tetramethyl-8-(2-propenyl)-, (3S,4R,5S,8R,9E,12S,14S,15R,16S,18R,19R,26aS), also known as FK506 as well as tacrolimus disclosed by EP 184162 and U.S. Pat. No. 4,894,366 is useful as an immunosuppressant. Another compound, 15,19-Epoxy-3H-pyrido[2,1-c][1,4]oxaazacyclotricosine-1,7,20,21(4H,23H)-tetrone, 8-ethyl-5,6,8,11,12,13,14,15,16,17,18,19,24,25,26,26a-hexadecahydro-5,19-dihydroxy-3-[(1E)-2-[(1R,3R,4R)-4-hydroxy-3-methoxycyclohexyl]-1-methylethenyl]-14,16-dimethoxy-4,10,12,18-tetramethyl-, (3S,4R,5S,8R,9E,12S,14S,15R,16S,18R,19R,26aS)-, also known as immunomycin as well as FK 520, disclosed in EPO Publication No. 0184162 is also useful as an immunosuppressant. Many other derivatives of these compounds as well as structural analogues have immunosuppressant property.

U.S. Pat. No. 5,508,398-discloses a process for separating a neutral non-polypeptide macrolide from acidic, basic and non-polar neutral impurities present in a concentrate of fermentation broth extracts or mother liquors containing said neutral macrolide which comprises in any order extraction step (a) and optionally one or both of steps (b) and (c), wherein (a) involves extraction with aqueous base, (b) involves extraction with aqueous acid and (c) involves treatment with non-aromatic hydrocarbon solvent.

U.S. Pat. No. 5,616,595 discloses a process for recovering water insoluble compounds (including FK506, FK520 and rapamycin) from a fermentation broth includes sequential steps of concentrating, solubilizing and diafiltering the compound of interest, all through a single closed recirculation system to recover the compound for further downstream purification.

Process for separation of tacrolimus from its related impurities is disclosed in U.S. Pat. No. 6,492,513. The process involves treatment of sulfonic acid group-containing ion exchange resin with silver ions. Alkenyl-side chain containing tacrolimus is separated from its alkyl-side chain containing analogs.

U.S. Pat. No. 6,576,135 discloses a process for similar separation. Tacrolimus along with the impurities is adsorbed to a nonionic adsorption resin followed by elution with an aqueous solvent containing silver ions.

Wang-Fan et. al. Reported a method for separation of tacrolimus from immunomycin using centrifugal counter-current chromatography. (Wang-Fan W., Kusters E., Lohse O., Mak C., Wang Y., Journal of Chromatography A, 864 (1999) 69-76).

The present invention is about a novel process for purification of macrolide compound. Here a easily scalable ammonia treatment is used to remove acidic impurities.

SUMMARY OF THE INVENTION

The instant invention relates to a novel process for purification of macrolide compounds.
The novel process of the instant invention comprises:
a) treatment of an impure or crude macrolide with water immiscible solvent,
b) optional concentration of the mixture,
c) treatment with ammonia gas to phase out impurities,
d) separation of impurities,
e) optional concentration of the phase containing the macrolide,
f) loading on silica chromatography, optionally reversed phase or pretreated with silver, and elution of the macrolide,
g) affording the macrolide in substantially pure form
h) optional repetition of step f and g to afford the macrolide in substantially pure form.

The thus obtained product is of pharmaceutically acceptable quality.

The novel process of the has several advantages like:
1. Industrially scalable
2. High purity product
3. Ease of operation
4. Less number of steps
5. Economic.

DETAILED DESCRIPTION OF THE INVENTION

As mentioned earlier, the instant invention relates to a novel process for the purification of macrolide compounds.
The novel process of the instant invention comprises:
a) treatment of an impure or crude macrolide with water immiscible solvent,
b) optional concentration of the mixture,
c) treatment with ammonia gas to phase out impurities,
d) separation of impurities,
e) optional concentration of the phase containing the macrolide,
f) loading on silica gel chromatography optionally reversed phase or pretreated with silver, and elution of the macrolide,
g) affording the macrolide in substantially pure form
a) optional repetition of step f and g to afford the macrolide in substantially pure form.

The macrolide of the present invention can be produced by fermentation, chemical synthesis or semi-synthetic process. The broth obtained by fermentation or aqueous phase containing macrolide can be directly extracted with water immiscible solvent. Any crude material in solid, semisolid or liquid form obtained either from broth, synthetic process or combination thereof can be treated with water immiscible solvent to effect solubilization of the macrolide into the water immiscible solvent. The water immiscible solvent containing the macrolide can be partially concentrated. The concentration can be affected by methods known per se. The concentration can be affected by vaporization of the solvent. The vaporization of the solvent can be carried out by heating without or with reduced pressure. The thus obtained mixture can be treated with ammonia gas. The impurities can be separated by methods known per se e.g. filtration, centrifugation or any suitable solid-liquid separation method. The macrolide-containing phase can be subjected to charcoalization. The macrolide-containing phase can be concentrated by method discussed earlier. The phase containing macrolide can be subjected to silica chromatography. The silica may be reversed phase. The silica gel may be pretreated with silver. The elute from the chromatography can be mixed with water immiscible solvent. The water immiscible solvent can be selected from a group comprising hydrocarbons, heterocyclic compounds, ethers or esters. Preferably the solvent is selected from hydrocarbons or ethers. The macrolide can be afforded by crystallization or precipitation. The macrolide can be afforded from single or mixture of solvents selected from ethyl acetate, diethyl ether, acetonitrile, and hexane.

The following examples further illustrate the invention, it being understood that the invention is not intended to be limited by the details disclosed therein.

EXAMPLES

Example 1

The fermentation broth (11 Kg) containing 1.2 g tacrolimus was extracted with 11 L of ethyl acetate. The ethyl acetate extract was partially concentrated to 1.2 L. The concentrate was chilled to 4° C. and ammonia was purged through the concentrate for 30 minutes. The solution was filtered using celite as filter aid to separate the precipitated impurities. The filtrate was concentrated to obtain 28 g oily residue. The residue was applied on a silica gel column. The column was washed with 3 column volumes of 25% ethyl acetate in hexane and 3 column volumes of 50% ethyl acetate in hexane. The product was eluted with 75% ethyl acetate in hexane. The product containing fractions were pooled and concentrated to obtain 2.8 g oily residue. The residue was dissolved in 100 ml ethyl acetate. 3 g of activated charcoal was added to it. The mixture was stirred for 20 minutes and then filtered. The filtrate was concentrated to obtain 2.7 g of oily residue. To the residue, 2.5 ml of ethyl acetate was added. The crude product was crystallized at 4° C. by slow addition of hexane. The crude product was filtered and dried.

The crude product was applied to a silica gel column. Silica gel (230-400 mesh) was initially treated with silver nitrate. The column was eluted with 75% ethyl acetate and 25% hexane. The product containing fractions were pooled and concentrated. The product was crystallized as mentioned earlier from ethyl acetate and hexane. The crystals were filtered and dried. The chromatographic purity was greater than 99%

Example 2

The fermentation broth (29 Kg) containing 3.1 g tacrolimus was extracted with 29 L of ethyl acetate. The ethyl acetate extract was partially concentrated to 2 L. The concentrate was chilled to 4° C. and ammonia was purged through the concentrate for 20 minutes. The solution was filtered using celite as filter aid to separate the precipitated impurities. The filtrate was concentrated to obtain 51 g oily residue. The residue was applied on a silica gel column. The column was washed with 3 column volumes of 25% ethyl acetate in hexane and 3 column volumes of 50% ethyl acetate in hexane. The product was eluted with 75% ethyl acetate in hexane. The product containing fractions were pooled and concentrated to obtain 6 g oily residue. The residue was dissolved in 200 ml ethyl acetate. 6 g of activated charcoal was added to it. The mixture was stirred for 20 minutes and then filtered. The filtrate was concentrated to obtain 5 g of oily residue. To the residue, 5 ml of ethyl acetate was added. The crude product was crystallized at 4° C. by slow addition of hexane. The crude product was filtered and dried.

The 3 g of the crude product was applied to a RP HPLC column (d~50 mm×H~200 mm) gel column. The product was eluted with n-butanol:acetonitrile:buffer in the ratio of 9.75: 12.5:77.75. The buffer contained 1.36 g/L potassium dihydrogen phosphate, 1 ml/L of triethyl amine, and 1 ml/L of phosphoric acid. The product containing fractions were pooled and extracted with equal volume of ethyl acetate. The ethyl acetate layer was dried with anhydrous sodium sulfate and was concentrated. The product was crystallized as mentioned earlier from ethyl acetate and hexane. The crystals (1.6 g) were filtered and dried. The chromatographic purity was greater than 99%.

We claim:

1. A novel process for the recovery of a macrolide in substantially pure form comprising:
   a) treating an impure or crude macrolide with water immiscible solvent to form a mixture,
   b) optionally concentrating the mixture,
   c) treating with ammonia gas to phase out impurities,
   d) separating impurities,
   e) optionally concentrating a phase containing the macrolide,
   f) loading on silica gel chromatography, wherein silica gel is optionally reversed phase or pretreated with silver, and eluding the macrolide,
   g) affording the macrolide in the substantially pure form,
   h) optionally repeating steps f and g to afford the macrolide in the substantially pure form.

2. The process as in claim 1, wherein the macrolide is a member selected from the group consisting of tacrolimus, immunomycin and sirolimus.

3. The process as in claim 1, wherein the water immiscible solvent is a member selected from the group consisting of hydrocarbons, heterocyclic compounds, ethers and esters.

4. The process as in claim 1, wherein the water immiscible solvents is a member selected from the group consisting of benzene, toluene, hexane, ethyl acetate, isobutyl acetate and butyl acetate.

5. The process as in claim 1, wherein the macrolide compound is afforded by crystallization or precipitation.

6. The process as in claim 1, wherein the crystallization is carried out using solvents selected from ethyl acetate, diethyl ether, acetonitrile, or hexane.

7. The process as in claim 1, wherein the macrolide is obtained by fermentation.

8. The process as in claim 1, wherein the macrolide is obtained by synthetic process.

9. The process as in claim 1, comprising:
   a) treating an impure or crude macrolide with water immiscible solvent to form a mixture,
   b) optionally concentrating the mixture,
   c) treating with ammonia gas to phase out impurities,
   d) separating impurities,
   e) optionally concentrating the phase containing the macrolide,
   f) loading on silica gel chromatography and elusion eluding the macrolide,
   g) optionally concentrating and mixing with the water immiscible solvent,
   h) affording macrolide in purer form,
   i) loading on silica gel chromatography pretreated with silver and eluding the macrolide,
   j) affording the macrolide in the substantially pure form.

10. The process as in claim 1, comprising:

a) treating an impure or crude macrolide with water immiscible solvent,
b) optionally concentrating the mixture,
c) treating with ammonia gas to phase out impurities,
d) separating impurities,
e) optionally concentrating the phase containing the macrolide,
f) loading on silica gel chromatography and eluding the macrolide,
g) optionally concentrating and mixing with water immiscible solvent,
h) affording macrolide in purer form,
i) loading on reversed phase silica chromatography and eluding the macrolide,
j) affording the macrolide in the substantially pure form.

* * * * *